(12) United States Patent
Reichert et al.

(10) Patent No.: US 7,992,843 B2
(45) Date of Patent: Aug. 9, 2011

(54) ANESTHETIC VAPORIZER

(75) Inventors: Dirk-Stefan Reichert, Lübeck (DE);
Karl-Ludwig Gippert, Lübeck (DE);
Thomas Lutter, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1057 days.

(21) Appl. No.: 11/778,202

(22) Filed: Jul. 16, 2007

(65) Prior Publication Data

US 2008/0066749 A1    Mar. 20, 2008

(30) Foreign Application Priority Data

Sep. 20, 2006   (DE) .......................... 10 2006 044 099

(51) Int. Cl.
*B01F 3/04*   (2006.01)
(52) U.S. Cl. .. 261/63; 261/74; 261/119.1; 261/DIG. 65; 128/203.25
(58) Field of Classification Search .................. 261/45, 261/54, 63, 72.1, 74, 119.1, DIG. 65; 128/203.25, 128/204.14
See application file for complete search history.

(56) References Cited

U.S. PATENT DOCUMENTS

| | | | | |
|---|---|---|---|---|
| 2,911,008 A * | 11/1959 | Du Bois | ................... | 137/625.31 |
| 2,941,528 A * | 6/1960 | Fabian et al. | ............ | 128/203.25 |
| 3,158,154 A * | 11/1964 | Schreiber | ................. | 128/203.25 |
| 3,298,674 A * | 1/1967 | Gilbertson | ..................... | 261/30 |
| 3,575,168 A * | 4/1971 | Jones et al. | .............. | 128/203.14 |
| 3,588,057 A * | 6/1971 | Breiling | ....................... | 261/39.1 |
| 3,756,577 A * | 9/1973 | Breiling | ......................... | 261/63 |
| 3,841,560 A * | 10/1974 | Sielaff | .......................... | 239/136 |
| 3,940,064 A * | 2/1976 | Takaoka | .......................... | 239/74 |
| 4,014,382 A * | 3/1977 | Heath | ............................. | 165/60 |
| 4,059,657 A * | 11/1977 | Hay | ............................ | 261/104 |
| 4,253,453 A * | 3/1981 | Hay | ......................... | 128/200.19 |

FOREIGN PATENT DOCUMENTS

DE   1 271 903   2/1969
DE   18 11 817   9/1976

* cited by examiner

*Primary Examiner* — Scott Bushey
(74) *Attorney, Agent, or Firm* — McGlew and Tuttle, P.C.

(57) ABSTRACT

A dispensing element of an anesthetic vaporizer is provided that can be manufactured in a simple manner and makes it possible to dispense anesthetic over a broad setting range. The dispensing element (11) includes two, longitudinally extending dispensing channels (14, 15), which are connected to one another in terms of flow by means of a connection channel (16). The gas flows from one of the dispensing channels (14) into the other dispensing channel (15) via the connection channel (16).

21 Claims, 4 Drawing Sheets

ANESTHETIC VAPORIZER

CROSS REFERENCE TO RELATED APPLICATIONS

This application claims the benefit of priority under 35 U.S.C. §119 of German Patent Application DE 10 2006 044 099.4 filed Sep. 20, 2006, the entire contents of which are incorporated herein by reference.

FIELD OF THE INVENTION

The present invention pertains to an anesthetic vaporizer with an evaporator chamber for enriching parts of a fresh gas with anesthetic vapor and with a dispensing element with a gas inlet and with a gas outlet for introducing anesthetic vapor into a gas channel and with a setting means at the dispensing element.

An anesthetic vaporizer of the type mentioned in the form of an anesthetic evaporator became known from DE-PS 12 71 903.

BACKGROUND OF THE INVENTION

In the prior-art anesthetic vaporizer, the gas flow is split into a bypass gas flow and an evaporator chamber gas flow after a gas inlet opening. The bypass gas flow flows via a bypass resistance to the outlet. The evaporator chamber gas flow is sent through an evaporator chamber, which is partly filled with liquid anesthetic, and is concentrated there to saturation while flowing past the surface of the anesthetic. Via a dispensing element, which is arranged downstream of the evaporator chamber, the evaporator chamber gas flow is again united with the bypass gas flow at a mixing site. The anesthetic concentration obtained at the mixing site or the gas discharge opening is obtained from the split ratio of the bypass gas flow to the evaporator chamber gas flow. The quantity of anesthetic vapor that is mixed with the gas flow is obtained from the saturation vapor pressure of the anesthetic and the split ratio of the bypass gas flow to the evaporator chamber gas flow.

The dispensing element downstream of the evaporator chamber is designed as a cone in a conical sleeve, forming a cone resistance, whose degree of opening can be changed with a setting element in the form of a setting wheel. The drawback of the prior-art dispensing element is that the cone resistance requires a considerable manufacturing effort, must be manufactured with high precision and must be guided with very high precision in order to obtain the desired scaling over an angle range of up to 300° in terms of the angle of rotation for the anesthetic concentration on the setting wheel.

An evaporation device for volatile anesthetics (anesthetic vaporizer), in which the anesthetic dispensing is carried out by means of manually rotatable dispensing plates and a ring groove, is known from DE-AS 18 11 817.

Such dispensing grooves must be manufactured with very high precision in order to meet the very high requirement on the accuracy of setting for the anesthetic concentration in case of small anesthetic vapor volumes, i.e., a low concentration setting. Furthermore, the scaling of the concentration marks that can be obtained with these dispensing grooves on the setting wheel with only a small angle of up to about 120° between the off position and the maximum concentration mark is disadvantageous. This leads to reduced precision of setting compared to the conical dispensing elements.

SUMMARY OF THE INVENTION

The basic object of the present invention is to show a dispensing element for an anesthetic vaporizer, which can be manufactured in a simple manner and makes possible a high accuracy of setting and a broad setting range.

According to the invention, an anesthetic vaporizer is provided comprising an evaporator chamber for enriching parts of the fresh gas with anesthetic vapor. A dispensing element is provided with a gas inlet and with a gas outlet for introducing anesthetic vapor into a gas channel. The dispensing element comprises two dispensing channels extending essentially radially and concentrically and a connection channel wherein the gas flow is directed through said dispensing channels from said gas inlet to said gas outlet via said connection channel. A setting means is provided at the dispensing element for changing at least one of an effective length and effective cross section of one or both of said dispensing channels between said gas inlet and said gas outlet.

The dispensing channels may be connected to one another in a U-shaped pattern. The dispensing channels may be arranged to extend circularly over a largest part of a circumference thereof and at nearly equal distance from one another. The cross-sectional area of said dispensing channels may advantageously be between 0.1 mm² and 20 mm². A cross-sectional area of at least one the dispensing channels may be designed such that the cross-sectional area expands in a wedge-shaped manner in the direction of flow or opposite thereto. At least one said dispensing channel may have a cross-sectional area changing with an angle of rotation.

The gas inlet and said gas outlet may be arranged stationarily in a housing. The gas channels may be displaceable in relation to the gas inlet and the gas outlet with the setting means. The gas inlet, the gas outlet and the dispensing channels may be arranged stationarily in a housing and the connection channel is designed as a connection channel displaceable/rotatable with said setting means in relation to the housing and said dispensing channels. The dispensing channels may also be arranged on a thin plate between the housing and a carrier plate with a connection channel. The cross-sectional area of the dispensing channels is such, in at least in one position of the setting means, that the gas flow through the dispensing channels is interrupted.

The advantage of the present invention is essentially that two dispensing channels in the form of grooves are provided as the dispensing element, which have either a constant or variable height or width along the direction of gas flow and are coupled with one another in terms of flow on one side by means of a connection channel. The dispensing channels extend extensively radially, concentrically with constant, but different radii. A setting range of more than 300° can thus be obtained, and the gas path that can be used for the dispensing is up to twice as long due to the dispensing channels extending in parallel, as a result of which the dispensing channels can be manufactured with acceptable tolerances.

The gas flow takes place here from a gas inlet of the dispensing element in a first dispensing channel and from there via the connection channel into the adjacent, second dispensing channel, the gas being drawn off in the second dispensing channel via a gas outlet.

Due to the use of two dispensing channels extending essentially in parallel, a substantially greater range of variation is obtained for varying the cross section of one dispensing channel or even of both dispensing channels in order to obtain different flow characteristics and hence different dosages and scalings. For example, the width of one or both of the dispensing channels may be left constant, while the depth is varied along the direction of flow. Furthermore, it is possible to change the cross section areas along the direction of flow in steps or in such a way that the cross section increases or decreases once and/or several times.

The cross-sectional area of a dispensing channel is on the order of magnitude of 0.1 mm² and 20 mm². A cross section equaling zero can be used to turn off the gas flow completely.

It is especially advantageous to arrange the gas inlet and the gas outlet stationarily in a housing. The dispensing channels are now milled as grooves into a carrier plate, which is rotatable/displaceable in relation to the gas inlet and the gas outlet. The angular position of the dispensing channels in relation to the gas inlet and the gas outlet can be changed by means of the setting wheel, and the effective length of the gas channels is either increased or decreased with the setting wheel.

The largest quantity of anesthetic vapor is dispensed when the gas/vapor flow being discharged from the evaporator chamber reaches the gas outlet of the dispensing element nearly directly from the gas inlet via the connection channel. The smallest quantity of anesthetic vapor is dispensed when flow takes place completely through both dispensing channels and the U-shaped connection channel is approximately in the middle of the gas path.

Provisions are made in an advantageous variant/exemplary embodiment of the dispensing element for arranging the gas outlet and the dispensing channels stationarily in a housing and for increasing or decreasing the effective length of the dispensing channels by means of a connection channel, which can be displaced or rotated in relation to the dispensing channels. The advantage of this variant in terms of manufacturing technology is that both the gas inlet and the gas outlet and the dispensing channels can be arranged on a single carrier plate and that only the connection channel must be connected to the carrier plate in a gas-tight and rotatable or displaceable manner.

Exemplary embodiments of the present invention are shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
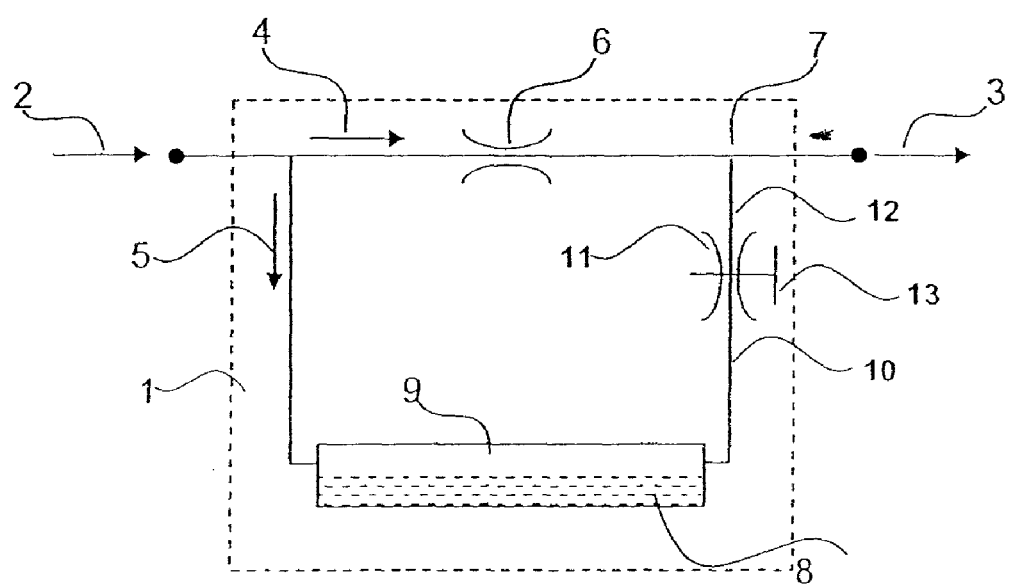
FIG. 1 is a schematic view showing the design of an anesthetic evaporator operating according to the bypass principle and including a dispensing element.

Referring to the drawings in particular, FIG. 1 schematically illustrates an anesthetic vaporizer 1 with a gas inlet opening 2 and with a gas outlet opening 3. The gas flow is split into a bypass gas flow 4 and an evaporator chamber gas flow 5 after the gas inlet opening 2.

The bypass gas flow 4 reaches the gas outlet opening 3 via a bypass resistance 6 and a mixing site 7.

The evaporator chamber gas flow 5 flows through an evaporator chamber 9 partially filled with anesthetic 8 above the liquid, it is enriched with anesthetic vapor up to saturation and reaches, from the gas inlet 10 of a dispensing element 11, via a gas outlet 12, a mixing site 7, where the gas flows 4, 5 unite.

The dispensing element 11 is coupled with the setting wheel 13 of the anesthetic vaporizer 1, with which the quantity of anesthetic vapor mixed with the bypass gas flow 4 can be changed.

Figure 2:
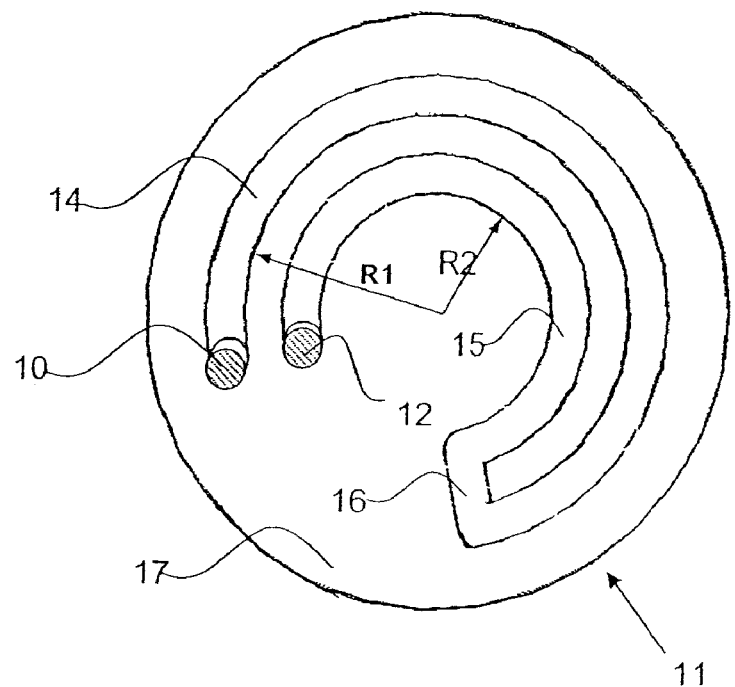
FIG. 2 is a partially sectional view of a first embodiment of a dispensing element according to the present invention in a position close to the minimum dosage.

FIG. 2 schematically shows the design of a first embodiment of a dispensing element 11 according to the present invention, which has a first dispensing channel 14 and a second dispensing channel 15. The dispensing channels 14, 15 extend along circular paths with different radii R1 and R2 and are connected to one another by a connection channel 16. The dispensing channels 14, 15 are milled as grooves into the carrier plate 17.

The gas inlet 10 and the gas outlet 12 are arranged stationarily on a housing, not shown more specifically, and the gas flow is from the gas inlet 10 to the gas outlet 12 via the first dispensing channel 14, the connection channel 16 and the second dispensing channel 15. Depending on the setting of the carrier plate 17 in relation to the stationary gas inlet 10 and the gas outlet 12, the effective length of the dispensing channels 14, 15 through which flow takes place is increased or decreased. The flow resistances of the bypass resistance 6 and of the dispensing channels 14, 15 are coordinated with one another such that the smallest volume flow of anesthetic vapor is dispensed via the dispensing channels 14 and 15 in the positions of the gas inlet 10 and gas outlet 12 in relation to the dispensing channels 14, 15, which are shown in FIG. 2.

Figure 3:
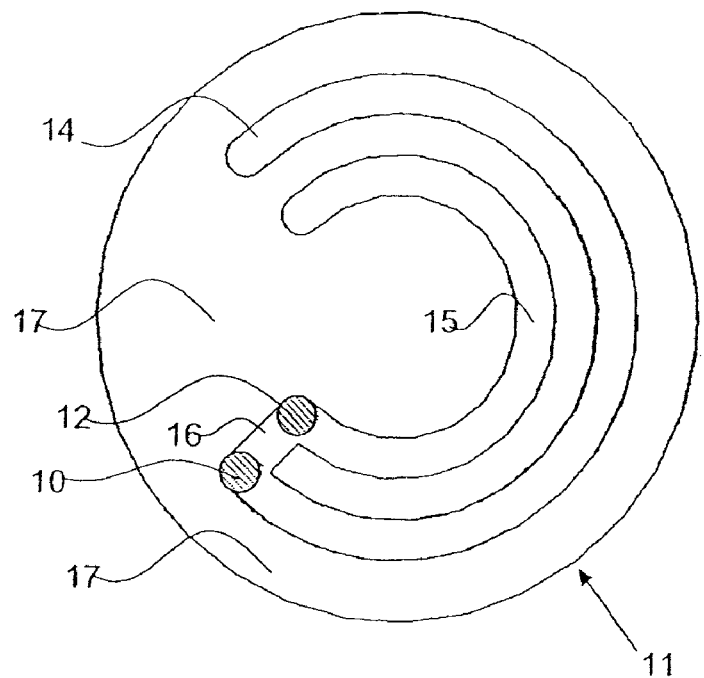
FIG. 3 is a partially sectional view showing the dispensing element according to FIG. 2 in a position close to the maximum concentration (dosage)

FIG. 3 schematically shows the position of the carrier plate 17 in relation to the gas inlet 10 and the gas outlet 12 in the case of the maximum quantity of anesthetic vapor. The gas enriched with anesthetic from the evaporator chamber flows here from the gas inlet 10 to the gas outlet 12 almost exclusively via the connection channel 16.

Figure 4:
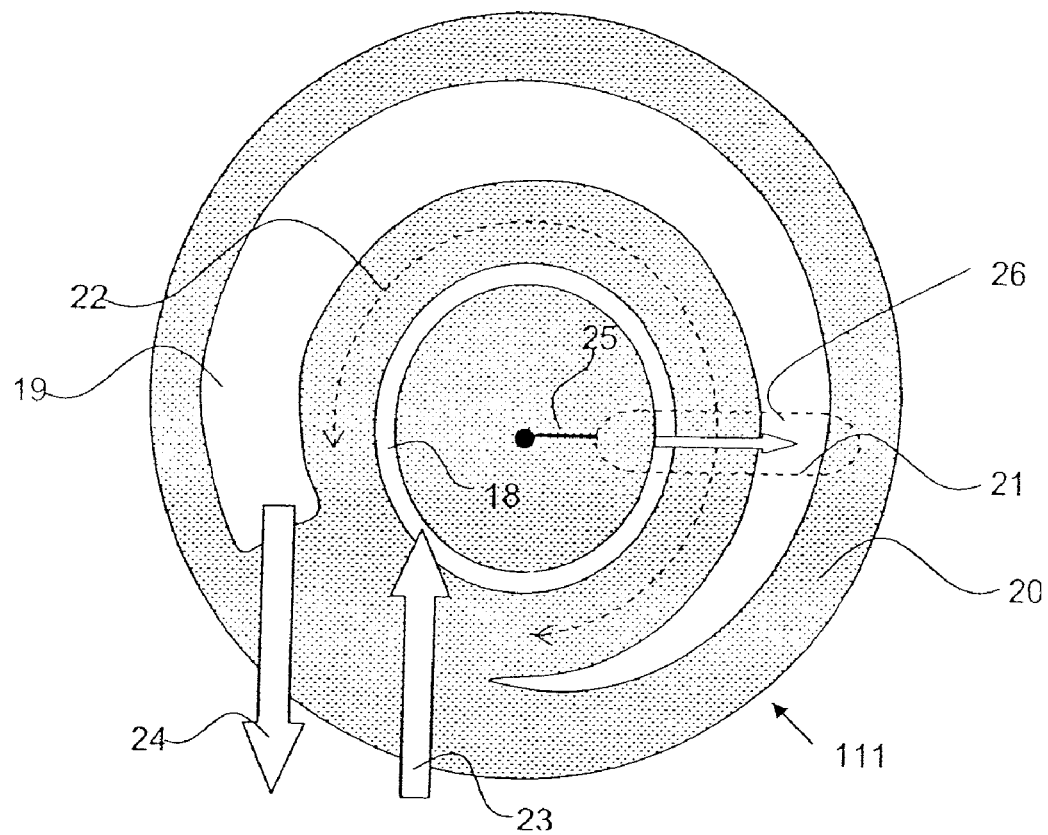
FIG. 4 is a sectional view showing a second embodiment of a dispensing element according to the present invention with a dispensing channel of variable cross section, with a second dispensing channel without change in cross section and with a connection channel displaceable in relation to the dispensing channels.

FIG. 4 schematically shows the design of a second embodiment of a dispensing element 111 according to the present invention with a third dispensing channel 18 and with a fourth dispensing channel 19 on a carrier plate 20. The two dispensing channels 18, 19 are connected to one another in terms of flow by means of a displaceable/rotatable connection channel 21 on a second carrier plate 26, which is shown only schematically. The third dispensing channel 18 is designed as a circular ring-shaped channel, at least on part of the circumference, and without contour or without an essential resistance in relation to dispensing. The fourth dispensing channel 19 has a cross-sectional area that extends over an angle of up to 340°.

The carrier plate 26 with the connection channel 21 can be pivoted by means of a setting wheel 25 along the arrow 22 and it now changes the position of the parts of the dispensing channels through which flow takes place. The gas flow through the second dispensing element 111 takes place via a gas inlet 23, the third dispensing channel 18, the connection channel 21 and the fourth dispensing channel 19 to the gas outlet 24. The fourth dispensing channel 19 is designed here such that the groove in the carrier plate 20 widens in height and width along the direction of flow.

Figure 5:
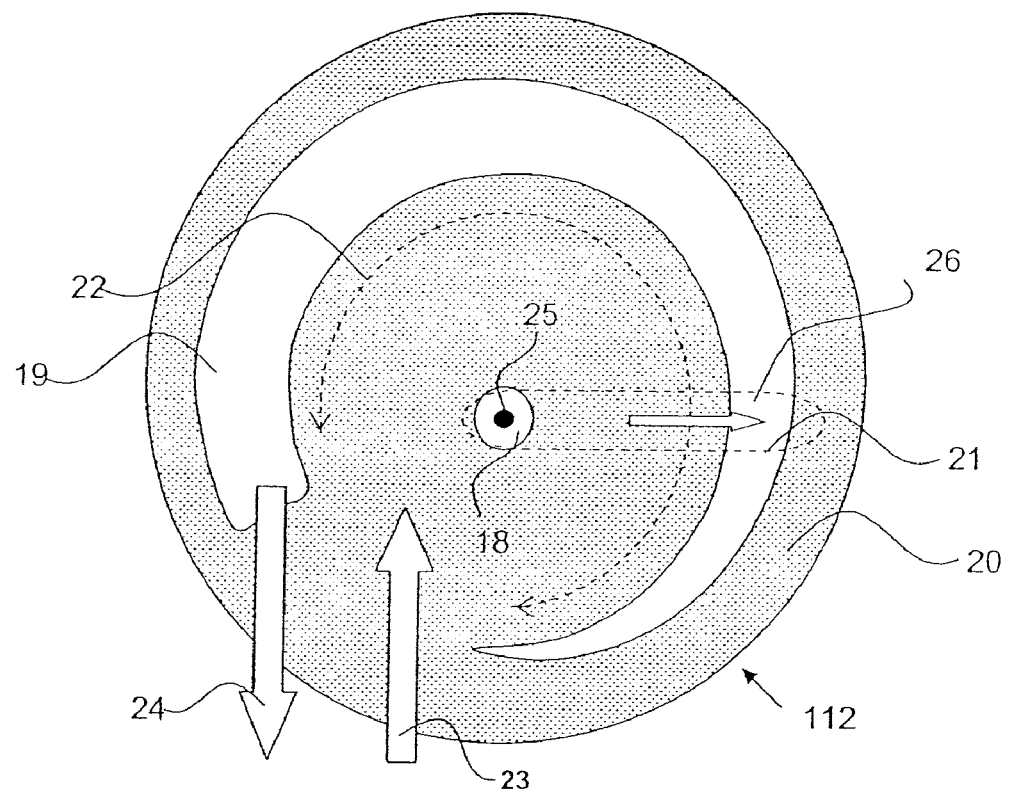
FIG. 5 is a sectional view showing the dispensing element similar to that according to FIG. 4, but in which a dispensing channel is instead provided as a central hole.

FIG. 5 schematically shows the design of a third embodiment of a dispensing element 112 according to the present invention with the third dispensing channel 18 and the fourth dispensing channel 19 on a carrier plate 20. The third dispensing channel 18 is degenerated, compared to FIG. 4, from a circular groove into a hole near the center. The fourth dispensing channel 19 and the carrier plate 26 with the connection channel 21 are designed corresponding to FIG. 4.

In a fourth embodiment of the dispensing element according to the present invention, which is not shown in the figures, the dispensing channels 18, 19 are not milled into the carrier plate 20, unlike in FIGS. 4 and 5, but they are placed as a thin plate between the carrier plate 26 and the housing with the gas inlet 23 and the gas outlet 24 and fixed against rotation/displacement. If variation of the height of the dispensing channels 18, 19 is eliminated, the plate may be prepared as a punched part or cut part simply from a thin foil. The plate may be made of a material that offers a better friction pair against anesthetic vapor.

While specific embodiments of the invention have been shown and described in detail to illustrate the application of the principles of the invention, it will be understood that the invention may be embodied otherwise without departing from such principles.

What is claimed is:

1. An anesthetic vaporizer comprising:
an evaporator chamber for enriching portions of fresh gas with anesthetic vapor;
a dispensing element with a gas inlet and with a gas outlet for introducing anesthetic vapor into a gas channel, said dispensing element comprising two dispensing channels extending essentially radially and concentrically and a connection channel wherein the gas flow is directed through said dispensing channels from said gas inlet to said gas outlet via said connection channel; and
a setting means at said dispensing element, said setting means changing at least one of an effective length and effective cross section of one or both of said dispensing channels between said gas inlet and said gas outlet.

2. An anesthetic vaporizer in accordance with claim 1, wherein said dispensing channels are connected to one another in a U-shaped pattern.

3. An anesthetic vaporizer in accordance with claim 1, wherein said dispensing channels extend circularly over a largest part of a circumference thereof and are arranged at nearly equal distance from one another.

4. An anesthetic vaporizer in accordance with claim 1, wherein the cross-sectional area of said dispensing channels is between 0.1 mm$^2$ and 20 mm$^2$.

5. An anesthetic vaporizer in accordance with claim 1, wherein a cross-sectional area of at least one said dispensing channel is designed such that said cross-sectional area expands in a wedge-shaped manner in the direction of flow or opposite thereto.

6. An anesthetic vaporizer in accordance with claim 1, wherein at least one said dispensing channel has a cross-sectional area changing with an angle of rotation.

7. An anesthetic vaporizer in accordance with claim 1, wherein said gas inlet and said gas outlet are arranged stationarily in a housing and said gas channels are displaceable in relation to said gas inlet and said gas outlet with said setting means.

8. An anesthetic vaporizer in accordance with claim 1, wherein said gas inlet, said gas outlet and said dispensing channels are arranged stationarily in a housing and said connection channel is designed as a connection channel displaceable/rotatable with said setting means in relation to the housing and said dispensing channels.

9. An anesthetic vaporizer in accordance with claim 7, wherein said dispensing channels are arranged on a thin plate between the housing and a carrier plate with a connection channel.

10. An anesthetic vaporizer in accordance with claim 1, wherein the cross-sectional area of said dispensing channels is such, in at least in one position of said setting means, that the gas flow through said dispensing channels is interrupted.

11. An anesthetic vaporizer comprising:
an evaporator chamber for enriching fresh gas with anesthetic vapor;
a gas inlet;
a gas outlet;
two dispensing channels and a connection channel, wherein fresh gas is directed through said evaporator chamber and through said dispensing channels and said connection channel from said gas inlet to said gas outlet, said two dispensing channels extending substantially radially and concentrically; and
a setting means for changing the flow characteristics of one or both of said dispensing channels between said gas inlet and said gas outlet to change a volume of flow passing through said dispensing channels to said gas outlet.

12. An anesthetic vaporizer in accordance with claim 11, wherein said dispensing channels are provided on a displaceable part moveable by said setting means in relation to said gas inlet and said gas outlet and each of said dispensing channels have a U-shape, with one radially inward of the other and connected to one another via said connection channel, whereby a movement of said displaceable part changes a path length of said dispensing channels from said gas inlet to said gas outlet.

13. An anesthetic vaporizer in accordance with claim 11, wherein said dispensing channels are provided on a displaceable part moveable by said setting means in relation to said gas inlet and said gas outlet and at least one of said dispensing channels has a flow path of varying cross section, whereby a movement of said displaceable part changes a path length of said dispensing channels from said gas inlet to said gas outlet.

14. An anesthetic vaporizer in accordance with claim 11, wherein the cross-sectional area of said dispensing channels is between 0.1 mm$^2$ and 20 mm$^2$.

15. An anesthetic vaporizer in accordance with claim 11, wherein a cross-sectional area of at least one said dispensing channel is designed such that said cross-sectional area expands in a wedge-shaped manner in the direction of flow or opposite thereto.

16. An anesthetic vaporizer in accordance with claim 13, wherein said at least one of said dispensing channels has a cross-sectional area changing with an angle of rotation.

17. An anesthetic vaporizer in accordance with claim 11, wherein said gas inlet and said gas outlet are arranged stationarily in a housing and said dispensing channels are displaceable in relation to said gas inlet and said gas outlet with said setting means.

18. An anesthetic vaporizer in accordance with claim 11, wherein said gas inlet, said gas outlet and said dispensing channels are arranged stationarily in a housing and said connection channel is designed as a connection channel displaceable/rotatable with said setting means in relation to the housing and said dispensing channels.

19. An anesthetic vaporizer in accordance with claim 17, wherein said dispensing channels are arranged on a thin plate between the housing and a carrier plate with a connection channel.

20. An anesthetic vaporizer in accordance with claim 11, wherein the cross-sectional area of said dispensing channels is such, in at least in one position of said setting means, that the gas flow through said dispensing channels is interrupted.

21. An anesthetic vaporizer in accordance with claim 11, wherein said setting means changes at least one of an effective length and an effective cross section of one or more of said two dispensing channels between said gas inlet and said gas outlet.

* * * * *